United States Patent
Levinson et al.

(10) Patent No.: US 10,786,182 B2
(45) Date of Patent: Sep. 29, 2020

(54) SYSTEM AND METHOD FOR PASSIVE REMOTE MONITORING OF PATIENTS' FINE MOTOR BEHAVIOR

(71) Applicant: The Joan and Irwin Jacobs Technion-Cornell Innovation Institute, New York, NY (US)

(72) Inventors: Yaron Levinson, New York, NY (US); Tsvi Tsadok, Tel Aviv (IL)

(73) Assignee: THE JOAN AND IRWIN JACOBS TECHNION-CORNELL INSTITUTE, New York, NY (US)

( * ) Notice: Subject to any disclaimer, the term of this patent is extended or adjusted under 35 U.S.C. 154(b) by 461 days.

(21) Appl. No.: 14/849,097

(22) Filed: Sep. 9, 2015

(65) Prior Publication Data

US 2017/0065211 A1    Mar. 9, 2017

(51) Int. Cl.
*A61B 5/11*    (2006.01)
*A61B 5/00*    (2006.01)

(52) U.S. Cl.
CPC .......... *A61B 5/1124* (2013.01); *A61B 5/1121* (2013.01); *A61B 5/6897* (2013.01); *A61B 5/7267* (2013.01)

(58) Field of Classification Search
None
See application file for complete search history.

(56) References Cited

U.S. PATENT DOCUMENTS

| | | |
|---|---|---|
| 6,167,258 A | 12/2000 | Schmidt et al. |
| 6,546,134 B1 | 4/2003 | Shrairman et al. |
| 7,594,050 B2 | 9/2009 | Tysowski |
| 7,991,929 B2 | 8/2011 | Tysowski |
| 8,296,485 B2 | 10/2012 | Tysowski |
| 8,643,648 B2 | 2/2014 | Heywood et al. |
| 8,838,513 B2 | 9/2014 | Sudharsan |
| 9,064,040 B2 | 6/2015 | Sudharsan |
| 2008/0242950 A1 | 10/2008 | Jung et al. |
| 2009/0144089 A1 | 6/2009 | Heywood et al. |
| 2009/0150992 A1 | 6/2009 | Kellas-Dicks et al. |
| 2009/0189791 A1 | 7/2009 | Brinton et al. |
| 2009/0281829 A1 | 11/2009 | Hansen et al. |
| 2012/0029910 A1 | 2/2012 | Medlock et al. |
| 2012/0098750 A1* | 4/2012 | Allen ............... G06F 3/023 345/169 |
| 2012/0197825 A1 | 8/2012 | Medlock et al. |

(Continued)

FOREIGN PATENT DOCUMENTS

WO    2014042878 A1    3/2014

OTHER PUBLICATIONS

The International Search Report and the Written Opinion for PCT/US2015/049163, ISA/RU: Moscow, Russia, dated May 12, 2016.

*Primary Examiner* — Sean P Dougherty
*Assistant Examiner* — Benjamin S Melhus
(74) *Attorney, Agent, or Firm* — M&B IP Analysts, LLC

(57) ABSTRACT

A system and method for assessing fine motor functions based on user input patterns. The method comprises collecting raw data related to at least an interaction of a user with a computing device; computing, based on the raw data, at least one biometric attribute; generating a session pattern based on the at least one biometric attribute; and generating using the session pattern and a decision model a scale index indicating a current condition of the fine motor functionality of the user data.

19 Claims, 5 Drawing Sheets

(56) References Cited

U.S. PATENT DOCUMENTS

| | | | |
|---|---|---|---|
| 2012/0214143 A1 | 8/2012 | Severson et al. | |
| 2012/0223889 A1 | 9/2012 | Medlock et al. | |
| 2012/0295550 A1 | 11/2012 | Wilson et al. | |
| 2013/0041857 A1 | 2/2013 | Medlock et al. | |
| 2013/0231188 A1 | 9/2013 | Berberich et al. | |
| 2013/0253912 A1 | 9/2013 | Medlock et al. | |
| 2013/0346090 A1 | 12/2013 | Brincat et al. | |
| 2014/0108994 A1 | 4/2014 | Medlock et al. | |
| 2014/0114889 A1 | 4/2014 | Dagum | |
| 2014/0297267 A1 | 10/2014 | Spencer et al. | |
| 2014/0317028 A1 | 10/2014 | Turgeman et al. | |
| 2014/0351741 A1 | 11/2014 | Medlock et al. | |
| 2014/0359515 A1 | 12/2014 | Medlock et al. | |
| 2015/0006192 A1 | 1/2015 | Sudharsan et al. | |
| 2015/0006456 A1 | 1/2015 | Sudharsan | |
| 2016/0035093 A1* | 2/2016 | Kateb | A61B 5/0042 382/131 |
| 2016/0262680 A1* | 9/2016 | Martucci | A61B 5/162 |
| 2016/0345908 A1* | 12/2016 | Samzelius | A61B 5/6897 |

* cited by examiner

SYSTEM AND METHOD FOR PASSIVE REMOTE MONITORING OF PATIENTS' FINE MOTOR BEHAVIOR

TECHNICAL FIELD

The present disclosure relates generally to motoric behavior, and more specifically to assessing fine and gross motor functions of users based on keystroke dynamics biometrics.

BACKGROUND

Neuromuscular and musculoskeletal disorders affect the nerves that control voluntary muscles such as, e.g., arm and leg muscles. Individuals experiencing neuromuscular disorders exhibit decreased communication between the nervous system and muscles, thereby leading to weakened muscles. Consequently, such individuals experience symptoms such as tremor, bradykinesia, rigidity of muscles, twitching, cramps, aches and pains, and joint and movement problems. Proper diagnosis of neuromuscular disorders is crucial to securing appropriate treatment and improving the outcome of the treatment.

Conventional means of testing for neuromuscular disorders include electromyography (EMG), which involves inserting a needle electrode directly into a muscle to determine electrical activity in the muscle. This electrical activity can be compared and interpreted in order to diagnose neurological and muscular disorders. Although a low-risk procedure, EMG presents risks of bleeding, infection, and nerve injury around the point of needle insertion. As a result, EMG diagnosis may be impracticable for individuals who have had an electrical medical device (e.g., a pacemaker) implanted and/or have hemophilia. Additionally, the procedure for diagnosing neurological disorders via EMG may be painful or otherwise inconvenient for patients.

Notably, many neuromuscular conditions involve impairment in the function of hands and/or fingers. Thus, the current art offers standardized tests for evaluation of neuromuscular disorders. In an embodiment, such tests include, for example, the 9-Hole Peg Test (9-HPT). In a 9-HPT test, the user (patient) is seated at a table with a small, shallow container holding nine pegs and a wood or plastic block containing nine empty holes. Upon receiving a "start" command, the patient picks up the nine pegs one at a time as quickly as possible, puts them in the nine holes, and, once they are in the holes, removes them again as quickly as possible one at a time, replacing them into the shallow container. The total time to complete the task is recorded. Two consecutive trials with the dominant hand are immediately followed by two consecutive trials with the non-dominant hand. Based on the test results, a score or scale is provided. The scale of the test is also standardized and can be combined based on other evaluations performed by the physician. For example, a unified Parkinson disease rating scale (UPDRS) is a standardized scale for evaluating disorders related to the Parkinson disease.

The disadvantages of current procedures for evaluating neuromuscular disorders are that they require the user to visit the clinics from time to time to assess only the current conditions of disease. As such, the user's conditions are not monitored on a daily basis. Consequently, such procedures cannot proactively predict any improvement or deterioration of the user's condition. In addition, as standardized tests are limited, their results cannot be analyzed to derive more accurate scales. Further, complex and prolonged tests cannot be performed during clinical visits.

It would therefore be advantageous to provide a solution that would overcome the deficiencies of the prior art by accurately determining fine motor function based on user gestures. It would be further advantageous if such a solution would allow for monitoring of changes in users' motor function over time.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments, and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "some embodiments" may be used herein to refer to a single embodiment or multiple embodiments of the disclosure.

Certain embodiments include a method for assessing fine motor functions based on user input patterns. The method comprises collecting raw data related to at least an interaction of a user with a computing device; computing, based on the raw data, at least one biometric attribute; generating a session pattern based on the at least one biometric attribute; and generating using the session pattern and a decision model a scale index indicating a current condition of the fine motor functionality of the user data.

Certain embodiments include a system for assessing fine motor function based on user input patterns. The system comprises a processor; and a memory, the memory containing instructions that, when executed by the processor, configure the system to: collect raw data, wherein the raw data includes at least one of: keystroke dynamics, a gesture, and a sensory signal; compute, based on the raw data, at least one biometric attribute; generate a session pattern based on the at least one biometric attribute; and generate using the session pattern and a decision model a scale index indicating a current condition of the fine motor functionality of the user data.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
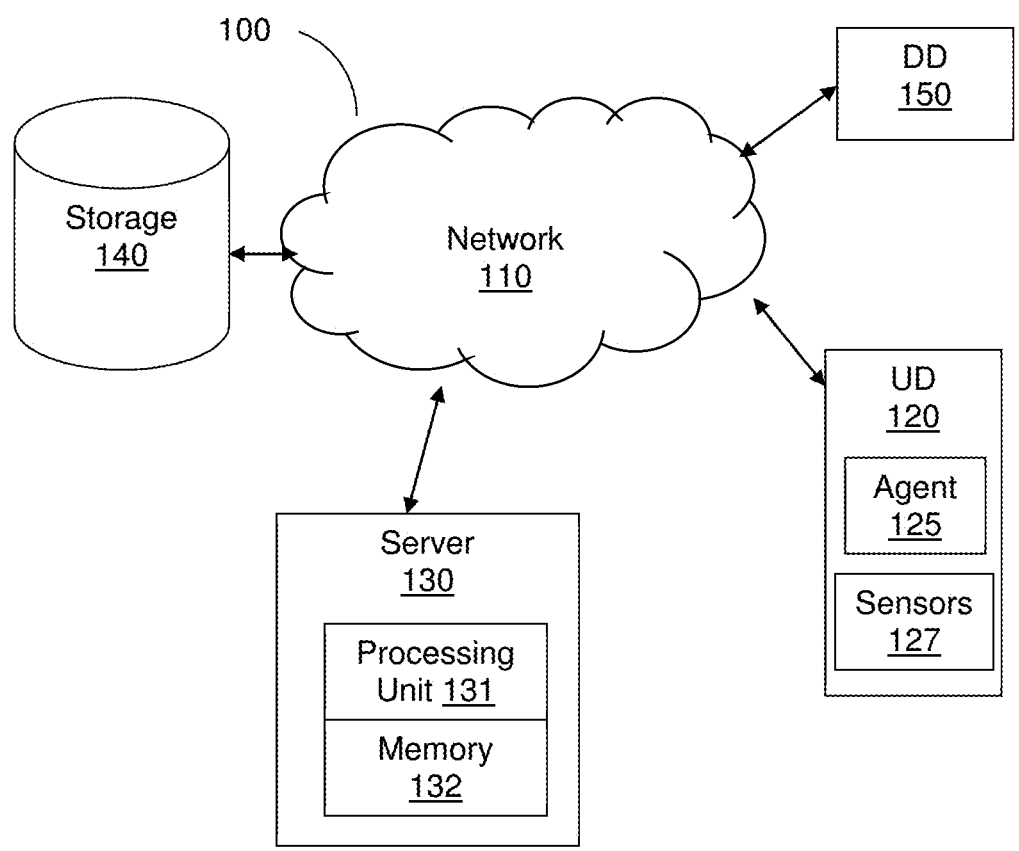
FIG. 1 is a schematic diagram of a network system used to describe the various disclosed embodiments.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

In an embodiment, the evaluation of fine motor functions is performed by analysis of keystrokes and/or gestures as entered by the user. Keystroke dynamics is the study of users' typing patterns on computer or smartphone keyboards. Typically, users tend to have unique habits when typing that become apparent during keystroke analysis. These unique habits may be used to verify an identity of a user by analyzing the user's keystrokes during typing. Changes in the keystroke dynamics may be used to detect changes in typing ability for a particular user. The changes in typing ability may be related to the individual's motor function, mental state, and/or cognitive state. The disclosed embodiments can be utilize to diagnose, monitor, and treat people suffering from Parkinson's Disease (PD), Multiple Sclerosis (MS), Rheumatoid Arthritis (AR), or any other diseases related to neuromuscular and musculoskeletal disorders.

FIG. 1 is an exemplary and non-limiting schematic diagram of a networked system 100 used to describe the various disclosed embodiments. The system 100 includes a user device (USD) 120, a server 130, a data warehouse 140, and a diagnostic device (DD) 150 communicatively connected to a network 110. The network 110 may be the Internet, the world-wide-web (WWW), a local area network (LAN), a wide area network (WAN), a metro area network (MAN), and the like. In an embodiment, the user device 120 may be, but is not limited to, a personal computer (PC), a personal digital assistant (PDA), a mobile phone, a smart phone, a tablet computer, a laptop, a wearable computing device, and the like.

The user device 120 is configured to execute at least one agent 125. The agent 125 may be, for example, a web browser, a script, an add-on, a mobile application ("app"), or any type of software application. The user device 120 also includes a plurality of sensors 127 that may include, but are not limited to, accelerometers, gyroscopes, motion sensors, and the like. The user device 120 is also equipped with a display, which may be a touch-screen display 121 and a keyboard 123. The keyboard 123 may be, but is not limited to a standard keyboard, a laptop keyboard, a flexible keyboard, a handheld keyboard, a thumb-sized keyboard, a soft (on-screen) keyboard, and a projection keyboard. In an embodiment, the agent 125 is configured to generate the on-screen keyboard. It should be noted that one user device 120, one agent 125, and one sensor 127 are illustrated in FIG. 1 merely for the sake of simplicity and without limitation on the generality of any of the disclosed embodiments.

In an embodiment, the diagnostic device (DD) 150 is utilized to interact with the server 130 to at least review results of the analysis. The results (scales) may be related to a user or group of users, a disease area, and so on. The diagnostic device 150 may be operated by a physician, a clinician, a caregiver, a researcher (e.g., of a pharmaceutical company), and so on. In an embodiment, the diagnostic device 150 may be, but is not limited to, a PC, a PDA, a mobile phone, a smart phone, a tablet computer, a laptop, a wearable computing device, or another kind of computing device equipped with browsing, viewing, listening, filtering, and managing capabilities that is enabled as described herein below.

According to the disclosed embodiments, the agent 125 is configured to collect raw data related to the interactions of a user with the user device 120. The collected raw data includes at least one of: keystroke dynamics, gestures, and sensory signals. Such raw data can be gathered from the operating system of the user device 120 or through various processes performed by the agent 125. The raw data may be collected each time the user interacts with the user device 120. In an embodiment, the raw data is collected per session (e.g., at a preconfigured time interval) or continuously as the user types.

In an embodiment, the keystroke dynamics include any key that was struck (or tapped), the coordinates within the key that the user taps, the time that each key is tapped, the length of time that each key was tapped for, the sequence in which different keys in the keyboard are tapped (e.g., first 'a' then 'b'), and so on. The keystroke dynamics can be collected from any type of keyboard that the device 120 is equipped with or from a keyboard provided by the agent 125.

The gestures collected by the agent 125 may include any on-screen gestures that are not associated with tapping on a keyboard. For example, a drag gesture may be detected with a response to drawing a geometric shape on the screen, unlocking a screen, dragging a notification, dragging an icon from one place to another, and so on. In an embodiment, coordinates and time data related to each gesture movement are collected (e.g., through the operating system of the device 120). The time may be from the beginning to the end of the movement. The sensory signals include, but are not limited to, angular rotational velocity measurement, linear acceleration of movement, variation around a pre-defined gesture, the orientation of the device 120, motion information related to a user holding the device 120 (walking, cycling, running, sitting, etc.), and so on. It should be noted that the sensory signals, when collected, can be associated with the gestures and keystroke dynamics. For example, the key taps are detected while the user is walking as determined by an accelerometer of the user device 120.

In an embodiment, the gestures captured by the agent 125 may include gestures captured by a camera, e.g., a camera installed on the user device 120. Gestures that may be captured by a camera may include physical movements of the user, such as slouching, tremors, arm movements, and the like. Based on the physical movements of the user, raw data representative of the physical movements may be collected. As a non-limiting example, such raw data may be related to, but not limited to, the steadiness of a user's limb while moving, steadiness of a user's hands, movement patterns of the user, and so on.

In an embodiment, the collected raw data is sent to the server 130 for further processing and may be stored in the data warehouse 140. The collected raw data may be provided with the server 130 or stored together with the identity of the user device 120. For example, a user name, a full name, and/or identification information may be stored as an identity. In another embodiment, the server 130 can also receive clinical background data related to a user or a group of users to perform the analysis. Such clinical background data can be provided by the user device 120, by the diagnostic device 150, or retrieved from the data warehouse 140.

According to various embodiments, the agent 125 may attempt to send the collected raw data to the server 130 upon conclusion of a session, at a regular time interval (e.g., every hour), when a sufficient amount of data is collected, and so on. In an embodiment, if the agent 125 cannot send the collected raw data to the server 130 (e.g., if there is no connection between the user device 120 and the server 130), the agent 125 may store the collected raw data locally on the user device 120. In a further embodiment, the agent 125 may continue to attempt to send the previously collected raw data to the server 130 at a later time and/or periodically thereafter until the raw data is successfully sent.

According to the disclosed embodiments, the server 130 is configured to generate a baseline pattern for each user or a group of users using the collected raw data. The baseline pattern can be updated from time to time. The server 130 is configured to compute based, in part, on a decision model a scale index for determining the neuromuscular condition of a user. The scale index can be computed or generated as a new set of raw data is received. The scale index can be sent to or accessed by the diagnostic device 150 through a GUI or API.

The various embodiments performed by the server 130 will be now described in more detail. First, a set of attributes (hereinafter "biometrics attributes") are computed based on the collected raw data. The biometrics attributes may be computed per session and include at least gesture biometrics, dwell time, flight time, offset, slip, auto-correction rate, autocomplete rate, touch-area, accelerometers energy, error rate, Fitts Model parameters, and the like. The gesture biometrics may include, but are not limited to, time, accuracy, and so on. Accuracy may include, but is not limited to, smoothness and variance. The smoothness is the energy level of second derivative of the gesture's path. Variance is the steadiness of the user while performing a gesture and may be a measure of the deviation of a user's gesture from a predetermined pattern. For example, the smoothness may demonstrate the ruggedness of the path drawn by the user's finger. The variance may demonstrate the deviation of the user's hand from a straight line when the user performs a gesture involving dragging or swiping (e.g., drawing a line that is 85 degrees and/or one inch off of the position of a predetermined horizontal line). Smoothness and gesture variance are described further herein below with respect to FIG. 2.

The dwell time is the time taken by the user to tap a key on the keyboard (e.g., the difference in time between when a finger tapped the key and when the finger is lifted from the key). In an embodiment, the dwell time is computed for each key in the keyboard. The flight time is the time difference between two taps on two different keys in the keyboard (e.g., the difference in time between when a finger lifted from a first key and when a finger tapped a second key). In an embodiment, the flight time is computed for every two keys in the keyboard (bi-gram).

The keystroke offset is computed as the difference in coordinates of where the finger tapped the key in the keyboard relative to the center coordinates of the key. The slip is the distance the finger moves over the keyboard (or screen) when tapping a specific key. That is, the slip is the distance between the coordinates of the tapping point ("TouchDown event") and the coordinates of the finger when the finger lifted from the screen ("TouchUp event"). In an embodiment, the number of key taps (or keystrokes) required for the user to write a word or phrase is counted. An auto-correction rate is the ratio between the number of times the auto-correction feature was used (e.g., 'teh' changed to 'the') and the number of key taps. An autocomplete rate is the ratio between the number of times the autocomplete feature was used (e.g., 'unive' changed to 'university') and the number of key taps.

The error rate may be computed, for example, as the ratio between the number of key taps and the number of characters in the word. Other values for the error rate may be utilized without departing from the disclosed embodiments. The Fitts Model parameters are computed using a mathematical function that provides the mapping of the distance between two keys and the typical time it takes the user's finger to move from one key to another.

Figure 2:
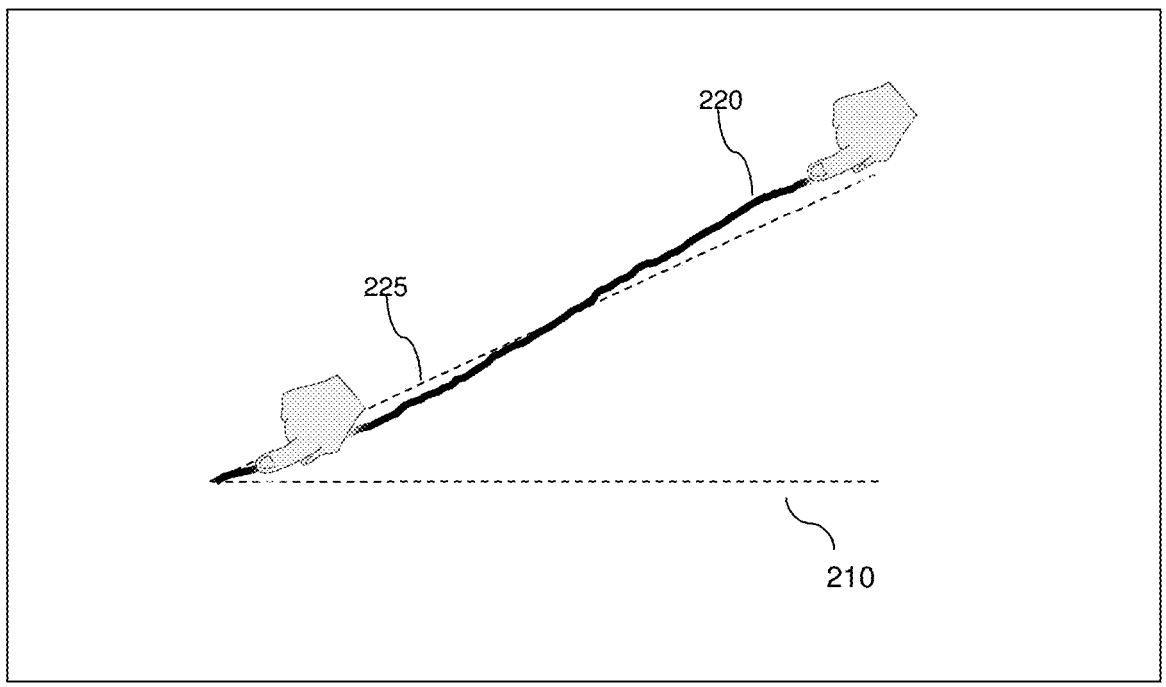
FIG. 2 is a schematic diagram demonstrating the gathering of gestures biometrics according to an embodiment.

In an embodiment, the gestures biometrics include time and accuracy of each detected gesture. As a non-limiting example, as shown in FIG. 2, a user draws a line 220 on a screen in an attempt to imitate a predetermined horizontal line pattern 210. Further, the variance is determined to be an average distance between points of the straight line pattern 225 and corresponding points of the drawn line 220.

Based on the biometrics attributes, a session pattern is generated. The session pattern is a collection of biometrics attribute measurements collected during a particular session. The baseline pattern is a set of session patterns collected during a predefined interval (e.g., a week, a month, etc.). Any of the session pattern or the baseline pattern may have a predefined format.

In an embodiment, the baseline pattern is utilized, in part, to train a decision model. The training can be also performed using multiple results gathered through "gold standard" tests, which benchmark tests based on a large sample size of users. The session patterns are input to the decision model based on the changes in between two or more session patterns and, relative to the training data set, a scale index is generated. The scale index may be in a format compliant with one or more standardized scales (e.g., UPDRs). In an embodiment, the generated scale index is a non-standardized scale. In an exemplary embodiment, the non-standardized scale is a numerical number (e.g., 1-10) indicating the severity of neuromuscular conditions. Alternatively, or collectively, the scale index provides a ratio between the biometrics attribute measurements (represented in the session pattern) and a non-standardized scale. This scale index allows physicians to correlate the measurements to known "gold standard" tests.

The decision model can be realized through, for example, a regression tree, a neural network (e.g., an artificial neural network), a support vector machine, and the like. An example for a decision model implemented according to an embodiment is described further herein below with respect to FIG. 3.

It should be noted that the server 130 typically comprises a processing unit 131 coupled to a memory 132. The processing unit 131 may comprise or be a component of a larger processing system implemented with one or more processors. The one or more processors may be implemented with any combination of general-purpose microprocessors, microcontrollers, digital signal processors (DSPs), field programmable gate arrays (FPGAs), programmable logic devices (PLDs), controllers, state machines, gated logic, discrete hardware components, dedicated hardware finite state machines, or any other suitable entities that can perform calculations or other manipulations of information.

The processing unit 131 may also include machine-readable media for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing system to perform the various functions described herein.

Figure 3:
FIG. 3 is a diagram illustrating the operation of a decision model according to an embodiment.

FIG. 3 shows an exemplary and non-limiting decision model 300 utilized according to an embodiment. The decision model 300 receives two inputs: a training data set 310 and session patterns 320. The decision model 300 outputs an index scale 330. As noted above, the index scale 330 may be a non-standardized scale or a standardized scale.

The collected training data set 310 includes a set of type patterns of various users or a specific user, labeled according to one or more gold standard scales. Label data refers to a validated or verified scale that can be associated with typing patterns. The label data may be provided, for example, by a physician, a clinician, a caregiver, a researcher, and the like. The label data associate a specific scale with any typing pattern based on the gold standard tests. The physician can diagnose a patient using one or more of the gold standard tests. Based on the diagnosis results, a standardized scale is provided. The typing patterns of a patient can be assigned with the provided standardized scale which is the label data. The purpose of the model is using the training data set (which includes the label data) is to predict the index scale 330 of the user based on the session patterns 320.

In an embodiment, new label data may be input to accompany the index scale 330 (e.g., data obtained when the user was examined in a clinic) to act as a feedback to the training set input 310 to improve the accuracy of the model. The decision model 300 is personalized to a specific user by being adapted based on training data captured from this specific user. As noted above, the decision model 300 may be implemented as, for example, a regression tree, a neural network (e.g., an artificial neural network), a support vector machine, and the like.

Figure 4:
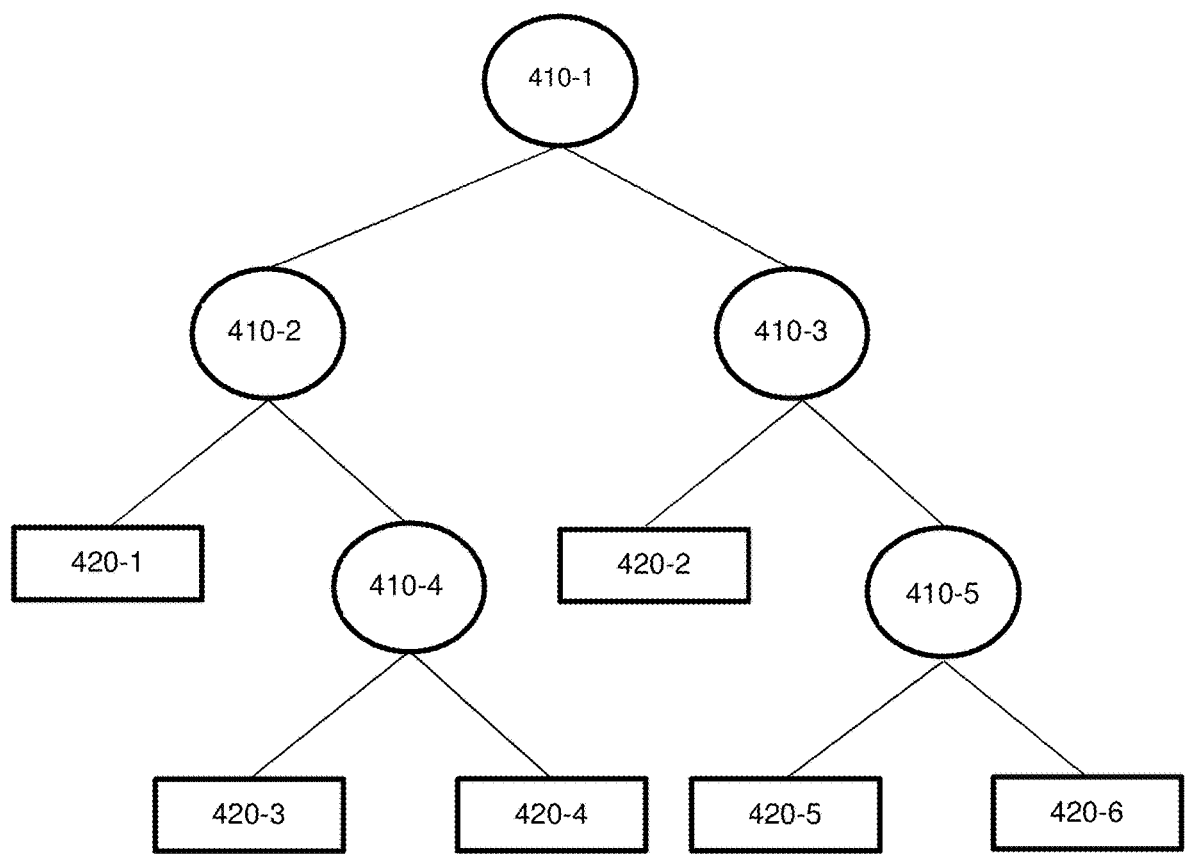
FIG. 4 is a decision model implemented using a regression tree implemented according to an embodiment.

FIG. 4 shows an exemplary and non-limiting decision model implemented using a regression tree 400 according to an embodiment. Each node 410 in the tree 400 is configured to compare an established value "V" to a session value "u". The established value may be a measurement of a biometrics attribute derived from the training data set, while the session value is a respective measurement from a particular session. For example, $V_1$ and $u_1$ of the node 410-1 may be dwell time measurements. The comparison made at each node 410 may be any one of: greater than, less than, equal to, not equal to, identical, and the like. The comparison may be performed on numerical values, Boolean values, strings, and so on.

Each of the leaves 420 of the tree 400 represents the index scale (such as, e.g., the index scale 330). That is, in order determine the index scale, the tree 400 is traversed from a root node 410-1 through the other nodes 410 until reaching a leaf 420. For example, the pairs of values <V1, u1>; <V2, u2>; and <V4, u4> are measurements of dwell time, flight time and offset, respectively, compared in the nodes 410-1, 410-2, and 420-4, respectively. If the comparisons made in nodes 410-1 and 410-2 show that the established value V1 is greater than the session value u1, that the established value V2 is less than the session value u2, and that the established value V4 is greater than the than the session value u4, than the leaf 420-3 provides a scale index of 10. On the other hand, if the comparisons made in node 410-4 shows that the established value V4 is less than the session value u4, than the leaf 420-4 provides a scale index of 7. In this example, the scale index is determined based on a scale from 1 to 10. If should be noted that the exemplary tree 400 includes only a few nodes 410 merely for the sake of simplicity and without limitation on the disclosed embodiments.

Figure 5:
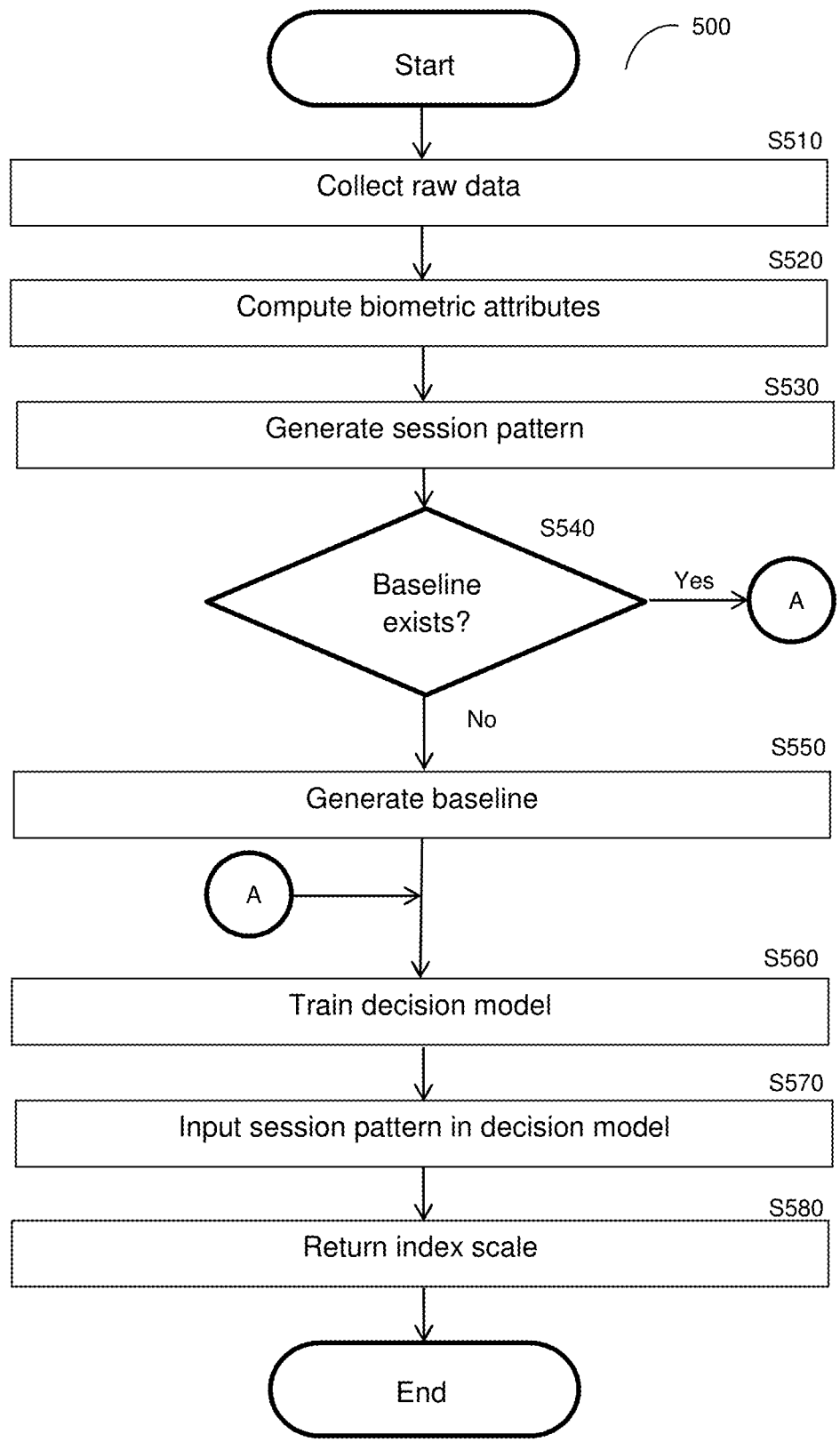
FIG. 5 is flowchart diagram illustrating a method for determining an index scale for fine motor functions according to an embodiment.

FIG. 5 is an exemplary and non-limiting flowchart diagram 500 illustrating a method for determining an index scale for fine motor functions according to an embodiment. In S510, raw data related to user inputs of a user is received. The collected raw data includes at least one of: keystroke dynamics, gestures, and sensory signals. In an embodiment, the raw data is collected per session (e.g., at a preconfigured time interval). In an embodiment, the keystroke dynamics include any key that was struck (or tapped), the coordinates within the key that the user taps, the time that each key is tapped, the length of time that each key was tapped for, the sequence in which different keys in the keyboard are tapped (e.g., first 'a' then 'b'), and so on.

The gestures collected include any on-screen gestures and/or gestures captured by a camera that are not associated with tapping on a keyboard. For example, a drag gesture may be detected with a response to drawing a geometric shape on the screen, unlocking a screen, dragging a notification, dragging an icon from one place to another, and so on. In an embodiment, coordinates and time data related to each gesture movement are collected (e.g., through the operating system of a user device). The time may be from the beginning to the end of the movement. The sensory signals include, but are not limited to, angular rotational velocity measurement, linear acceleration of movement, the orientation of the user device, motion information related to a user holding the device 120 (walking, cycling, running, sitting, etc.), and so on. It should be noted that the sensory signals, when collected, can be associated with the gestures and keystroke dynamics.

In S520, biometric attributes are computed based on the collected raw data. The biometrics attributes may be computed per session and include, but are not limited to, gesture biometrics, dwell time, offset, flight time, slip, error rate, and Fitts Model parameters. The gesture biometrics may include, but are not limited to, time, accuracy, and so on. Biometrics attributes are described further herein above with respect to FIG. 1.

In S530, a session pattern is generated based on the biometric attributes. The session pattern is a collection of biometrics attribute measurements collected during a particular session. The session pattern may have a predefined format.

In S540, it is checked whether a baseline pattern for the user exists. If so, execution continues with S560; otherwise, execution continues with S550. In S550, a baseline pattern is generated for the user. The baseline pattern is a set of session patterns collected during a predefined interval (e.g., a week, a month, etc.). The baseline pattern may have a predefined format.

In S560, a decision model is trained based on any of typing patterns and label data. As noted above, the typing patterns may be collected for a group of users or a specific user that the model is programmed for. As noted above, the label data provides an association between a standardized scale and the training data.

The decision model includes a scale index for determining the neuromuscular or musculoskeletal condition of a user. The scale index can be computed or generated as a new set of raw data is received. The decision model can be realized through, for example, a regression tree, a neural network (e.g., an artificial neural network), a support vector machine, and the like.

In S570, upon detection of a change between the generated session pattern and at least one previous session pattern, the generated session pattern is input into the decision model. Relative to the training set and the generated session pattern, a scale index is generated and output by the decision model. The scale index may be in a format compliant with one or more standardized scales (e.g., UPDRs). In an embodiment, the generated scale index is a non-standardized scale. In an exemplary embodiment, the non-standardized scale is a numerical number (e.g., 1-10) indicating the severity of neuromuscular and/or musculoskeletal conditions. Alternatively or collectively, the scale index provides a ratio between the biometrics attribute measurements (represented in the session pattern) and a non-standardized scale. This scale index allows physicians to correlate the measurements to known "gold standard" tests. In S580, the scale index that was output by the decision model is returned.

In an embodiment, new label data may be introduced to act as additional feedback to the training set input to improve the accuracy of the decision model. The new label data is related to a specific user that the model is programmed for. The new label data may be received, for example, when the user is diagnosed by a physician. The scale provided by the physician respective of the diagnosis is the new data set.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A method for assessing fine motor function based on user input patterns, comprising:
    training a decision model based on a training data set including a collection of training biometric attributes of a group of first users and label data associated with the collection of training biometric attributes, wherein the label data associates the training biometric attributes with a standardized scale, wherein the decision model is a machine learning model trained using supervised machine learning;
    collecting raw data related to at least an interaction of a second user with a computing device;
    receiving new label data at predetermined intervals, wherein the new label data is based on the interaction of the second user with the computing device, wherein the new label data indicates a new scale provided for the second user during an examination;
    updating the decision model using the new label data as feedback to improve the accuracy of the decision model with respect to the second user, wherein updating the decision model using the new label data as feedback further comprises using the new label data and training data captured from the second user during the examination as inputs to train the decision model;
    computing, based on the raw data, at least one biometric attribute;
    generating a session pattern based on the at least one biometric attribute; and
    generating, using the session pattern and the decision model, a scale index indicating a current condition of the fine motor function of the user data.

2. The method of claim 1, wherein the raw data includes at least one of: keystroke dynamics, a gesture, and a sensory signal.

3. The method of claim 2, wherein the keystroke dynamics are at least one of: any struck key, coordinates within a key, a time that each key is tapped, a length of time that a key was tapped for, an area of touch on a screen, and a sequence of key taps.

4. The method of claim 2, wherein the raw data includes the gesture, wherein the gesture is any of: drawing a geometric shape on a screen, unlocking a screen, dragging a notification, dragging an icon, and a gesture capture by a camera.

5. The method of claim 2, wherein the keystroke dynamics include the sensory signal, wherein the sensory signal is any of: angular rotational velocity measurement, linear acceleration of movement, an orientation of a device, and motion information related to the user holding a device.

6. The method of claim 1, wherein the biometric attributes are any of: gesture biometrics, dwell time, offset, flight time, slip, error rate, and Fitts Model parameters.

7. The method of claim 1, wherein the scale index is in a format compliant with at least one of the at least one standardized scale.

8. The method of claim 1, wherein the decision model is any of: a regression tree, a decision tree, a neural network, and a support vector machine.

9. The method of claim 1, wherein the new scale is provided based on the examination, wherein the new scale is provided based on a diagnosis of the second user.

10. The method of claim 1, wherein the new scale is a verified scale associated with the training data captured from the second user during the examination.

11. A system for assessing fine motor function based on user input patterns, comprising:
    a processor; and
    a memory, the memory containing instructions that, when executed by the processor, configure the system to:
    train a decision model based on a training data set including a collection of training biometric attributes of a group of first users and label data associated with the collection of training biometric attributes, wherein the label data associates the training biometric attributes with a standardized scale, wherein the decision model is a machine learning model trained using supervised machine learning;

collect raw data related to at least an interaction of a second user with a computing device;

receive new label data at predetermined intervals, wherein the new label data is based on the interaction of the second user with the computing device, wherein the new label data indicates a new scale provided for the second user during an examination;

update the decision model using the new label data as feedback to improve the accuracy of the decision model with respect to the second user, wherein updating the decision model using the new label data as feedback further comprises using the new label data and training data captured from the second user during the examination as inputs to train the decision model;

compute, based on the raw data, at least one biometric attribute;

generate a session pattern based on the at least one biometric attribute; and generating, using the session pattern and the decision model, a scale index indicating a current condition of the fine motor function of the user data.

12. The system of claim 11, wherein the raw data includes at least one of: keystroke dynamics, a gesture, and a sensory signal.

13. The system of claim 12, wherein the keystroke dynamics are at least one of: any struck key, coordinates within a key, a time that each key is tapped, a length of time that a key was tapped for, an area of touch on a screen, and a sequence of key taps.

14. The system of claim 12, wherein the raw data includes the gesture, wherein the gesture is any of: drawing a geometric shape on a screen, unlocking a screen, dragging a notification, dragging an icon, and a gesture capture by a camera.

15. The system of claim 12, wherein the keystroke dynamics include the sensory signal, wherein the sensory signal is any of: angular rotational velocity measurement, linear acceleration of movement, an orientation of a device, and motion information related to the user holding a device.

16. The system of claim 11, wherein the biometric attributes are any of: gesture biometrics, dwell time, offset, flight time, slip, error rate, and Fitts Model parameters.

17. The system of claim 11, wherein the scale index is in a format compliant with at least one of the at least one standardized scale.

18. The system of claim 11, wherein the decision model is any of: a regression tree, a decision tree, a neural network, and a support vector machine.

19. A non-transitory computer readable medium having stored thereon instructions for causing one or more processing units to execute a process, the process comprising:

training a decision model based on a training data set including a collection of training biometric attributes of a group of first users and label data associated with the collection of training biometric attributes, wherein the label data associates the training biometric attributes with a standardized scale, wherein the decision model is a machine learning model trained using supervised machine learning;

collecting raw data related to at least an interaction of a second user with a computing device;

receiving new label data at predetermined intervals, wherein the new label data is based on the interaction of the second user with the computing device, wherein the new label data indicates a new scale provided for the second user during an examination;

updating the decision model using the new label data as feedback to improve the accuracy of the decision model with respect to the second user, wherein updating the decision model using the new label data as feedback further comprises using the new label data and training data captured from the second user during the examination as inputs to train the decision model;

computing, based on the raw data, at least one biometric attribute;

generating a session pattern based on the at least one biometric attribute; and generating, using the session pattern and the decision model, a scale index indicating a current condition of the fine motor function of the user data.

* * * * *